Figure 1:
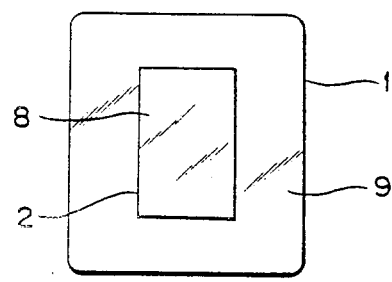
Figure 2:
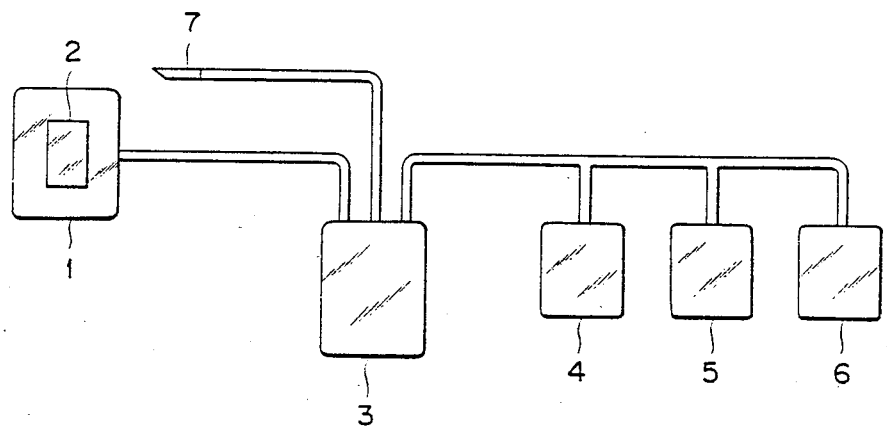

United States Patent [19]

Bott et al.

[11] Patent Number: 4,889,950

[45] Date of Patent: Dec. 26, 1989

[54] PREPARATION OF CARBOXYLIC ESTERS

[75] Inventors: Kaspar Bott, Mannheim; Horst Hartmann, Boehl-Iggelheim; Josef Guth, Ludwigshafen, all of Fed. Rep. of Germany

[73] Assignee: BASF Aktiengesellschaft, Ludwigshafen, Fed. Rep. of Germany

[21] Appl. No.: 235,610

[22] Filed: Aug. 24, 1988

[30] Foreign Application Priority Data

Aug. 25, 1987 [DE] Fed. Rep. of Germany ....... 3728242

[51] Int. Cl.$^4$ .............................................. C07C 69/52
[52] U.S. Cl. .................................... 560/205; 560/147; 560/226
[58] Field of Search ........................ 560/147, 226, 205

[56] References Cited

U.S. PATENT DOCUMENTS 4,250,328  10/1981  Fujita et al. ........................ 560/205
4,435,594   3/1984  Matsumura et al. ................ 560/205
4,748,268   5/1988  Dietsch et al. ...................... 560/205

*Primary Examiner*—Paul J. Killos
*Attorney, Agent, or Firm*—Keil & Weinkauf

[57] ABSTRACT

Carboxylic esters are prepared by reacting carboxylic acids with low-boiling alcohols by charging the reaction mixture to a 1st distillation column, withdrawing the reaction components carboxylic ester, water and unconverted alcohol as overhead product and charging this overhead product to a 2nd distillation column, from which (a) the overhead product comprises the alcohol or an azeotropic mixture of alcohol and water or alcohol and esteer, this overhead product being recycled into the esterification reaction (b) a liquid side product comprising carboxylic ester and water is withdrawn from the stripping section and separated in a phase separating vessel into water and carboxylic ester and the carboxylic ester is returned into the distillation column below the side takeoff point, and (c) the bottom product removed is the carboxylic ester.

4 Claims, 1 Drawing Sheet

PREPARATION OF CARBOXYLIC ESTERS

The present invention relates to a process for preparing carboxylic esters by reacting carboxylic acids with low-boiling alcohols.

For an industrial production of carboxylic esters, hereinafter simply referred to as esters, from carboxylic acids and alcohols to be commercially successful it is crucial that either or both o the reaction products, ester and water, be removable from the reaction mixture by distillation in order thereby to shift the ester equilibrium as far as possible in the desired direction. However, such a procedure is difficult when low-boiling alcohols such methanol or ethanol are used as reactants, since in this case the alcohol in question, or a mixture thereof with the ester formed, is frequently the most low-boiling component of the reaction mixture. In addition, low-boiling alcohols have little suitability for removing the water by azeotropic distillation, since in the presence of water they are incapable of forming two liquid phases from which the water is easily separable. The problems associated with the removal of water can be circumnavigated by using a circulating agent in the distillation. The use of such circulating agents has been extensively described in the technical literature, for example in Houben-Weyl, Methoden der Organischen Chemie, 4th edition, volume VIII, pages 522 and following.

The use of a circulating agent in the esterification of carboxylic acids with low-boiling alcohols is in general associated with additional separating operations which can have an adverse effect on the economics of the process.

It is an object of the present invention to esterify carboxylic acids with low-boiling alcohols such as methanol or ethanol as completely as possible without having to use a nonreactant for separating off the water.

We have found that this object ia achieved according to the invention when the reaction mixture is charged to a 1st distillation column and the reaction components carboxylic ester and water and unconverted alcohol are withdrawn as the overhead product and charged to a 2nd distillation column from which (a) the overhead product taken comprises the alcohol or an azeotropic mixture of alcohol and water or alcohol and ester, this overhead product being recycled into the esterification reaction, (b) a liquid side product comprising carboxylic ester and water is withdrawn from the stripping section and separated in a phase separating vessel into water and carboxylic ester and the carboxylic ester is returned into the distillation column below the side takeoff point, and (c) a bottom product removed is the carboxylic ester.

Further features of the invention form the subject matter of subclaims.

The present process ia particularly suitable for continuous operation and, what is more, can also be extended to the esterification of carboxylic acids which additionally contain a small amount of a low-boiling component as an impurity. An example thereof is the preparation of methyl halocarboxylates from methanol and a technical grade halocarboxylic acid which is contaminated with the halogen-free carboxylic acid. In this case, the impurity accumulates as the methyl carboxylate in the overhead product of the 2nd distillation column and can be withdrawn from there together with the recycled methanol.

Suitable alcohol/carboxylic acid pairs for which the process according to the invention is suitable are for example methanol/methacrylic acid, methanol/bromoacetic acid, methanol/bromopropionic acid, methanol/butyric acid, methanol/2-chlorobutyric acid, methanol/4-chlorobutyric acid methanol/2-bromoisobutyric acid, methanol/thioglycolic acid, methanol/crotonic acid, methanol/sorbic aci , methanol/2-mercaptopropionic acid, methanol/mercaptobutyric acid, ethanol/2-chloropropionic acid, ethanol/2-bromopropionic acid, ethanol/2-chlorobutyric acid, ethanol/2chloroisobutyric acid, ethanol/4-chlorobutyric acid and ethanol/2-bromoisobutyric acid.

The process according to the invention will be further illustrated hereinafter by reference to the drawing.

Reference numeral 1 designates a carboxylic acid $R^1\text{-}CO_2H$ and 2 a low-boiling alcohol $R^2\text{-}OH$ which are made to react in reaction vessel 3. In a rectifying column 4 the resulting reaction mixture, a mixture 5 of ester $R^1CO_2R^2$, water and unconverted alcohol $R^2OH$ is separated off overhead and charged into the distillation column 6 where further separation takes place as follows:

(a) An overhead product 7 comprising alcohol or an azeotropic mixture of alcohol and water or alcohol and ester is separated off and recycled into the reaction vessel, (b) a side product 8 comprising eater and water is taken from the stripping section and subsequently separated in the phase separating vessel 9 into a lighter phase 10 (ester in Example 1) and a heavier phase 11 (water in Example 1), the ester being recycled into the distillation column below the side takeoff point, and (c) a bottom product is separated off comprising ester 12.

The experimental apparatus as per the drawing comprised a 2-liter reaction vessel 3 upon which sat a rectifying column 4 whose diameter was 50 mm and whose fill level was 600 mm. The packing comprised 5 mm glass Raschig rings. Distillation column 6, which was likewise 50 mm in diameter, had the following parts, fill levels and types packing:

(a) rectifying section, 400 mm, 5 mm mesh wire rings
(b) upper stripping section down to the side takeoff point, 1200 mm, 5 mm glass Raschig rings and
(c) lower stripping section up to the side takeoff point, 500 mm, 5 mm glass Raschig rings.

EXAMPLE 1

Under steady state plant conditions the reaction vessel was charged per hour with 625 g of methacrylic acid, 235 g of fresh methanol, 122 g of recycled methanol and 17.4 g of recycled methyl methacrylate. The hourly discharge from the phase separating vessel as bottom phase comprised 130 g of water, 3.6 g of methyl methacrylate and 2.7 g of methanol. The bottom product of the 2nd distillation column comprised 722 g of methyl methacrylate per hour. The splitting ratio for the side takeoff was about 0.6. The reflux ratio for the rectifying column was about 0.5 and that of the 2nd distillation column about 13. The average residence time of the reaction mixture in the reaction vessel was 1.5 hours. The catalyst used comprised 50 g of sulfuric acid.

The 1.7 g/h missing in the mass balance are customary losses.

We claim:

1. A process for preparing a carboxylic ester by reacting a carboxylic acid with a low-boiling alcohol, which comprises charging the reaction mixture to a 1st distillation column, withdrawing the reaction components carboxylic ester, water and unconverted alcohol, but not unreacted carboxylic acid, as overhead product and charging this overhead product to a 2nd distillation column, from which
   (a) the overhead product comprises the alcohol or an azeoester, this overhead product being recycled into the esterification reaction,
   (b) a liquid side product comprising carboxylic ester and water is withdrawn from the stripping section and separated in a phase separating vessel into water and carboxylic ester and the carboxylic ester is returned into the distillation column below the side takeoff point, and
   (c) the bottom product removed is the carboxylic ester.

2. A process for preparing a carboxylic ester as set forth in claim 1, wherein the carboxylic acid used in the esterification is an unsaturated carboxylic acid of from 3 to 7 carbon atoms.

3. A process for preparing a carboxylic ester as set forth in claim 1, wherein the carboxylic acid used in the esterification reaction is a halocarboxylic acid or mercaptocarboxylic acid of from 2 to 5 carbon atoms.

4. A process for preparing a carboxylic ester as set forth in claim 1, wherein the halocarboxylic acid used in the esterification is contaminated with its halogen-free parent compound.

* * * * *